United States Patent [19]

Broadbent et al.

[11] Patent Number: 5,677,166
[45] Date of Patent: Oct. 14, 1997

[54] COMPOSITIONS AND METHODS FOR PHAGE RESISTANCE IN DAIRY FERMENTATIONS

[75] Inventors: Jeff R. Broadbent, Smithfield; Craig J. Oberg, Liberty; Shelby Caldwell, Syracuse, all of Utah

[73] Assignee: Utah State University, Office of Technology Commercialization, Logan, Utah

[21] Appl. No.: 462,017

[22] Filed: Jun. 5, 1995

[51] Int. Cl.$^6$ .................................................. C12N 1/20
[52] U.S. Cl. ............................ 435/252.3; 435/252.9; 435/853
[58] Field of Search ........................... 435/252.3, 252.9, 435/853

[56] References Cited

PUBLICATIONS

Arber et al. (1985) in: Basic Life Sciences, ed. Hollaender, v. 30, Plasmids in Bacteria, eds. Helinski, Cohen, Clewell, Jackson, Hollaender, pp. 21–31. (Plenum Press, New York and London).

Tsai (1986) Dissertation Abstracts International, B, 47, p. 2308. Abstract of Thesis, Oregon State Univ., USA.

Morita et al. (1991) Agricultural and Biological Chemistry, 55, 2871–2873.

Kim et al. (1992) Journal of Applied Bacteriology, 72, 201–207.

de Vos et al. (1994) Fems Micribiology Reviews, 15, 217–237.

Primary Examiner—Robert A. Wax
Assistant Examiner—Elizabeth Slobodyansky
Attorney, Agent, or Firm—Thorpe North & Western, L.L.P.

[57] ABSTRACT

A latococcal- and streptococcal-phage-resistant starter culture for fermenting milk comprises a food-grade bacterium from the genera Pediococcus, Leuconostoc, Lactococcus, Streptococcus, or Lactobacillus transformed with a genetic element containing genes for a lactose fermentation phenotype. A method of making a lactococcal-phage-resistant starter culture comprises transforming a non-lactose fermenting, food-grade bacterium with a genetic element carrying determinants for a lactose fermentation phenotype. A method of making cheese with lactococcal-phage-resistant starter culture is also disclosed.

11 Claims, 2 Drawing Sheets

COMPOSITIONS AND METHODS FOR PHAGE RESISTANCE IN DAIRY FERMENTATIONS

BACKGROUND OF THE INVENTION

This invention relates to phage resistant bacteria and methods of use thereof for dairy fermentations. More particularly, the invention relates to transformation of a phage-resistant, non-lactose-fermenting, food-grade bacterium with a genetic element that confers a lactose fermentation phenotype and methods of use thereof for fermenting milk and especially for making cheese. This genetically engineered bacterium is resistant to the limitations on growth and acid production caused by phages that infect the bacteria heretofore used in dairy fermentations and cheesemaking.

Production of cheese and cultured dairy products has long relied on the fermentation of milk by acid-producing bacteria. These bacteria are directly responsible for the acid development, flavor production, and other characteristics in dairy fermentations. Because the bacteria are so important to the outcome of the fermented product, great precautions are taken to ensure that starter cultures of the bacteria are robust and uncontaminated by undesirable microorganisms or bacteriophages. The fermentation process, however, is carried out in open vats in a nonsterile medium, pasteurized milk, and is thus highly vulnerable to contamination. The majority of strains of lactic acid-producing bacteria used in commercial production can be contaminated within a day or two of introduction into a factory by lytic bacteriophages capable of curtailing growth and acid production.

Historically, the bacteria used in starter cultures for cheese making, for example, were undefined mixtures of bacteria that were maintained and propagated in cheese factories. The bacteria in these starter cultures were in dynamic equilibrium wherein introduction of phages that attacked the bacteria was offset by selection of bacteria that were resistant to attack. These cultures worked moderately well in continuous use under the conditions used in small factories. Modern circumstances require larger production capacity and increased efficiency than were needed previously. These requirements have resulted in large volumes of milk being processed, fermentation vats being filled again soon after they are emptied, and processing times being shortened. To accomplish this increased production and efficiency, starter cultures presently contain defined mixtures of bacteria that are capable of uniform and rapid rates of acid production. These starter cultures are selected and propagated under aseptic conditions such that the bacteria are never exposed to phages until they reach the factory. Thus, modern practices have resulted in an increased probability of phage proliferation in the factory.

Several methods have been developed to minimize the detrimental effects of bacteriophage contamination during commercial dairy fermentations. Starter cultures can be protected from bacteriophage infection by use of concentrated cultures (e.g., U.S. Pat. Nos. 4,115,199 and 5,128,260), sterile bulk starter vessels, and phage-inhibitory media (e.g., U.S. Pat. No. 4,282,255). After inoculation of fermentation vats, however, phage contamination cannot be prevented. Rotation with bacterial strains that display resistance to different types of bacteriophage should, in principle, minimize development of bacteriophage populations. In practice, however, identification of strains with completely different patterns of phage sensitivity has proved difficult, and only a small number of such strains are available. Further, due to the rapidity that new phages arise that are able to overcome phage resistance of bacterial strains, new phage resistant bacteria have been merely a short term solution to the problem.

Several mechanisms of phage resistance have been identified. L. L. McKay et al., 47 Appl. Environ. Microbiol. 68 (1984), describes a plasmid-borne determinant of resistance to phage c2 that is thought to involve a temperature-sensitive DNase. M. E. Sanders et al., 47 Appl. Environ. Microbiol. 979 (1984), discloses that resistance of *Lactococcus lactis* ssp. *lactis* ME2 results from multiple temperature-sensitive mechanisms including prevention of phage adsorption, a restriction-modification system, and suppression of phage development. Some of the genetic determinants of these mechanisms are plasmid-borne, but others are chromosomal. M. E. Sanders et al., 46 Appl. Environ. Microbiol. 1125 (1983), teaches that *L. lactis* ssp. *lactis* ME2 contains a plasmid, pME0030, that codes for a function that prevents phage adsorption. M. E. Sanders et al., 42 Appl. Environ. Microbiol. 944 (1981), discloses that a plasmid in *L. lactis* ssp. *cremoris* KH codes for a restriction-modification system that provides resistance to phage c2. C. F. Gonzalez et al., 49 Appl. Environ. Microbiol. 627 (1985), describes transconjugants of matings of *S. lactis* SLA 2.24 or SLA 3.15 and *L. lactis* ssp. *lactis* biovar diacetylactis SLA 3.10 or SLA 3.23 that exhibit temperature-independent phage resistance not due to adsorption or restriction in phage growth. U.S. Pat. No. 4,883,756 to Klaenhammer et al. discloses phage resistance in some group N streptococci can be attributed to plasmid-borne restriction-modification systems. U.S. Pat. No. 5,139,950 to Klaenhammer et al. discloses plasmid-borne phage resistance to group N streptococci that includes genetic determinants for a heat-sensitive phage resistance property in certain backgrounds, such as *S. lactis* LM0230, and a heat-resistant phage resistance property in certain other backgrounds, such as *S. cremoris* strains HP, M43a, 924, KH, and TDM1.

Japanese Patent Publication JP 3175978 A, published Jul. 31, 1991, describes synthesis of lactose fermenting bacteria produced by cell conjugation between Pediococcus sp. and a Lactococcus or Streptococcus sp. The resulting strain carries an antibiotic resistance marker and is, thus, disadvantageous for use in food for human consumption.

In view of the foregoing, it will be appreciated that providing bacteriophage-resistant bacteria and/or starter cultures, methods of use thereof in dairy fermentations, and methods of producing phage-resistant bacteria and starter cultures would be a significant advancement in the art.

OBJECTS AND SUMMARY OF THE INVENTION

It is an object of the present invention to provide phage-resistant bacteria for fermenting milk.

It is another object of the invention to provide a method of genetically engineering bacteria to make a phage-resistant starter culture for dairy fermentations.

It is still another object of the invention to provide a method of making cheese with a phage-resistant starter culture produced by genetic engineering of bacteria.

These and other objects are achieved by providing a phage-resistant starter culture for fermenting milk comprising a food-grade bacterium transformed with and operable for replicating a genetic element bearing a genetic locus for lactose fermentation, wherein the bacterium expresses a lactose fermentation phenotype. The food-grade bacterium is preferably a member selected from the group consisting of *Pediococcus acidilactici, P. dextrinicus, P. inopinatus, P. halophilus, P. damnosus, P. pentosaceus, Leuconostoc cremoris, L. citrovorum, L. dextranicum,* and *L. mesenteroides.* The genetic element preferably encodes lactose-specific components of a lactococcal phosphotransferase system, such as the lactococcal phosphotransferase system from *Lactococcus lactis,* contains no antibiotic resistance marker, and is a member selected from the group consisting of a plasmid, cosmid, phagemid, lysogenic virus, non-lytic virus, transposable element, and mixtures thereof. It is more preferable that the genetic element is a plasmid, such as the 55 kb plasmid, pTSL, pTSLP, and derivatives thereof.

A phage-resistant bacterium for fermenting milk comprises a food-grade bacterium transformed with and operable for replicating a genetic element bearing a genetic locus for lactose fermentation, wherein the food-grade bacterium transformed with the genetic element expresses a lactose fermentation phenotype.

A method of making a phage-resistant starter culture for fermenting milk comprises transforming a food-grade bacterium with a genetic element bearing a genetic locus for lactose fermentation, wherein the transformed food-grade bacterium is operable for replicating the genetic element and expresses a lactose fermentation phenotype.

A method of making mozzarella cheese comprises the steps of:

(a) pasteurizing cow's milk having a fat content in the range of about 1.5 to 3.5% by weight;

(b) fermenting the milk with a starter culture comprising a food-grade bacterium transformed with and operable for replicating a genetic element bearing a genetic locus for lactose fermentation, wherein the bacterium expresses a lactose fermentation phenotype, to obtain a cheese milk;

(c) coagulating the cheese milk to obtain a coagulum comprised of curd and whey;

(d) cutting the coagulum and draining the whey therefrom, thereby leaving a cheese curd;

(e) heating, kneading, and stretching the cheese curd until it is a homogeneous, fibrous mass having a moisture content in the range of about 45 to 60% by weight and a milkfat content of at least about 30% by weight on a dried solids basis;

(f) placing the mass in a bath of cold brine and leaving it there long enough to achieve cooling and salt penetration;

(g) removing the cooled cheese from the brine to obtain an unripened cheese; and (h) aging the unripened cheese until taste, texture, and baking properties develop.

DETAILED DESCRIPTION OF THE INVENTION

Figure 1:
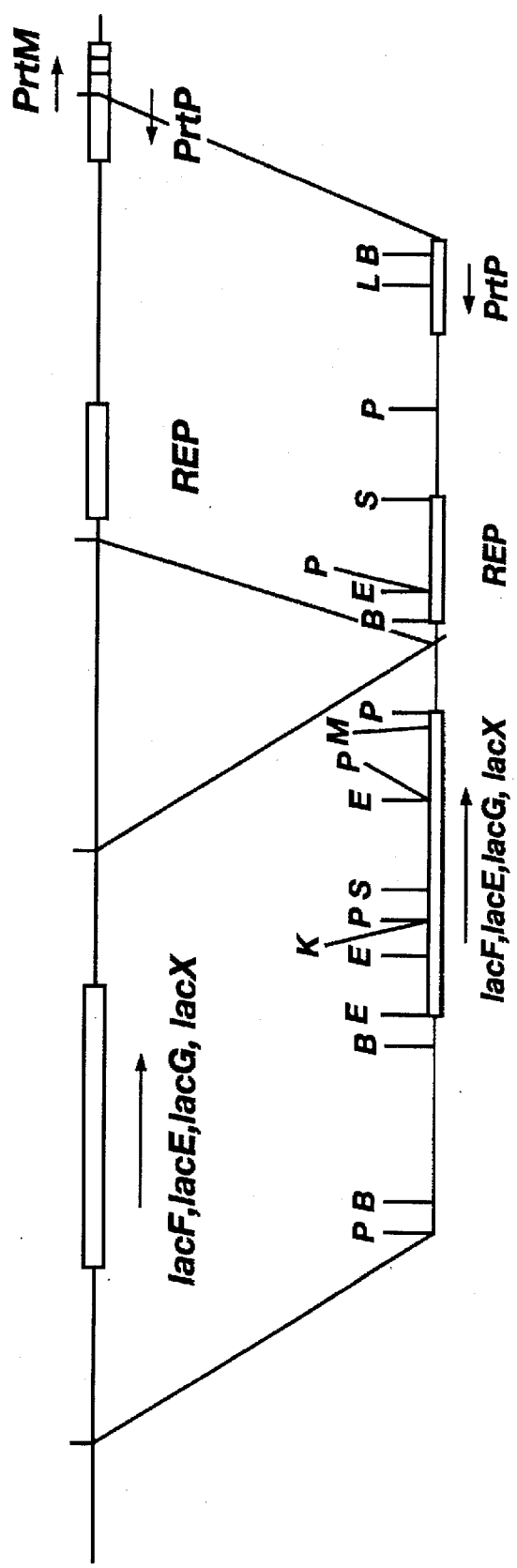
FIG. 1 shows a restriction map of pTSL: L—BglI, B—BglII, E—BstEII, K—KpnI, M—MluI, P—PstI, S—StuI. The top line is a schematic representation of the 55 kb lactococcal lactose plasmid from *L. lactis* C2. The slanting lines identify regions of the 55 kb plasmid that are retained in its deletion derivative, pTSL.

Before the present phage resistant bacteria and methods of use thereof in dairy fermentations are disclosed and described, it is to be understood that this invention is not limited to the particular process steps and materials disclosed herein as such process steps and materials may vary somewhat. It is also to be understood that the terminology employed and examples described herein are used for the purpose of describing particular embodiments only and are not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a starter culture containing "a bacterium" includes a mixture of two or more such bacteria, reference to "a plasmid" includes reference to one or more of such plasmids, and reference to "a gene" includes reference to two or more of such genes.

In describing and claiming the present invention, the following terminology will be used in accordance with the definitions set out below.

As used herein, "phage resistance" means a measurable inhibition of infection or proliferation by lactococcal or streptococcal phages. As used herein, "lactococcal phage" means phage that infects *Lactococcus lactis* strains used in commercial dairy fermentations, and "streptococcal phage" means phage that infects *Streptococcus thermophilus.* As will be described in more detail below, the method of obtaining phage resistance according to the present invention involves use of food-grade bacteria from species and genera other than those used for dairy fermentations and genetic engineering of such bacteria for ability to ferment lactose. The mechanisms of phage resistance used by these food-grade bacteria can include, but are not limited to, morphological differences from susceptible bacteria, differences in receptors or attachment sites, restriction-modification systems, and the like.

As used herein, "food-grade bacteria" means bacteria that are used and generally regarded as safe for use in fermenting food, that lack a lactose fermenting phenotype, and that are phylogenetically distinct from *Lactococcus lactis* and *Streptococcus thermophilus* used for fermenting milk and are thus naturally resistant to lactococcal and streptococcal phages. Food-grade bacteria include species from the genera Pediococcus, Lactococcus, Streptococcus, Leuconostoc, and Lactobacillus. Such bacteria are not susceptible to lactococcal or streptococcal phages. Preferred food-grade bacteria are *P. acidilactici, P. dextrinicus, P. inopinatus, P. halophilus, P. damnosus, P. pentosaceus, Leuconostoc cremoris, L. citrovorum, L. dextranicum,* and *L. mesenteroides.*

As used herein, "genetic element" means a nucleic acid operable for carrying genetic information. A genetic element can, without limitation, be double- or single-stranded or a combination thereof, DNA or RNA or a combination thereof, and can be in the form of a plasmid, cosmid, phagemid, other extrachromosomal element, lysogenic or non-lytic virus, insertion sequence, transposon or other transposable element, or mixture thereof. A genetic element used in the present invention should not contain an antibiotic resistance marker since the presence of such antibiotic resistance markers in food for human consumption is disadvantageous and to be avoided, as is known in the art.

As used herein, a "derivative" of a genetic element means any deletion variant, insertion variant, or combination deletion/insertion variant of such genetic element that is capable of replication, maintenance, transcription, and translation in a food-grade bacterium such that a lactose fermentation phenotype is expressed.

As used herein, "lactose fermentation phenotype," "Lac$^+$," "lactose positive," and similar terms mean the ability to ferment lactose and utilize lactose as a sole carbon source, resulting in the production and release of acid. Similarly, "Lac$^-$," "lactose negative," and similar terms mean the lack of ability to ferment lactose.

As used herein, "transformation" means introduction of a genetic element into a bacterium by a chemical and/or physical process that is not a naturally occurring phenomenon. Thus, for example, transformation includes insertion of a genetic element into a bacterium by calcium-dependent transformation techniques, heat shock, electroporation, and combinations thereof and similar methods that accomplish the same result. This definition of transformation specifically excludes naturally occurring phenomena such as conjugation, transduction, and infection. Transformation can result in the genetic element being maintained as an extra-chromosomal element or being integrated into the bacterial chromosome.

As shown in the references cited and briefly reviewed above, an approach taken in the prior art to overcome the problem of susceptibility of acid-producing bacteria used in dairy fermentations to phages encountered in such fermentations has been to identify plasmids that bear genetic determinants for phage resistance and transfer those plasmids into the traditionally used Lac$^+$ lactococci, resulting in phage-resistant lactococci. What has not been recognized in the references is that phages tend to infect only certain bacteria that are closely related strains or species. In other words, bacteria are generally resistant to phages that infect phylogenetically distant species or genera. In this invention, food-grade bacteria other than streptococci or lactococci are used for their natural resistance to infection by streptococcal or lactococcal phages, which are the phages that are present in fermentation plants and that halt bacterial growth and acid production in dairy fermentations. Such naturally phage-resistant, Lac$^-$, food-grade bacteria are rendered Lac$^+$ according to the present invention by transformation with a genetic element that carries a genetic locus for a Lac$^+$ phenotype. The result is phage-resistant food-grade bacteria that are capable of fermenting lactose and of being used in dairy fermentations.

Suitable food-grade bacteria that can be transformed with a Lac$^+$ genetic element include bacteria of the genera Pediococcus, Lactococcus, Streptococcus, Leuconostoc, and Lactobacillus. Preferred species of bacteria include *P. acidilactici, P. dextrinicus, P. inopinatus, P. halophilus, P. damnosus, P. pentosaceus, L. cremoris, L. citrovorum, L. dextranicum*, and *L. mesenteroides*.

Plasmids pTSL and pTSLP are naturally-occurring 35 kb deletion derivatives of a 55 kb *Lactococcus lactis* plasmid that encodes lactose-specific components of the *L. lactis* phosphotransferase system (PTS), and genes for the lactococcal extracellular proteinase. L. L. McKay et al., Transductional evidence for plasmid linkage of lactose metabolism in *Streptococcus lactis* C2, 32 Appl. Environ. Microbiol. 45 (1976). Sequence analysis of loci required for these properties has shown that the *L. lactis* lac operon includes genes for Enzyme III$^{lac}$ (lacF), Enzyme II$^{lac}$ (lacE), phospho-β-galactosidase (lacG), and enzymes for the utilization of galactose-6-phosphate (lacA-D). W. M. De Vos & E. E. Vaughn, Genetics of Lactose Utilization in Lactic Acid Bacteria, 15 FEMS Microbiol. Rev. 217–37 (1994). Production of the extracellular proteinase requires two genes, prtP that encodes the proteinase and prtM that produces a processing enzyme needed for protein maturation. J. Kok, Genetics of the proteolytic system of lactic acid bacteria, 87 FEMS Microbiol. Rev. 15 (1990). A region of the plasmid containing the origin of replication (REP) has also been identified. M. J. Gasson et al., Molecular genetics of metabolic traits in lactic streptococci, in *Streptococcal Genetics* 242–45 (J. J. Ferretti & R. Curtiss III eds. 1987). FIG. 1 shows a restriction map of pTSL and its relationship to the 55 kb lactococcal lactose plasmid from *L. lactis* C2.

Restriction analysis of the naturally occurring deletion derivatives of the 55 kb plasmid, such as pTSL and pTSLP, has demonstrated that deletions may involve genes for lactose fermenting ability, proteinase production, or both. M. J. Gasson et al., Molecular genetics of metabolic traits in lactic streptococci, in *Streptococcal Genetics* 242–45 (J. J. Ferretti & R. Curtiss III eds. 1987). FIG. 1 illustrates that all of prtM and the amino terminus-encoding portion of prtP were lost in the deletion event that gave rise to pTSL. Consequently, cells containing pTSL do not produce the extracellular proteinase, but are Lac$^+$. In contrast, phenotypic analysis of lactococcal transductants that contain pTSLP indicates that both the lactose and proteinase genes are preserved on this plasmid. Plasmids pTSL, pTSLP, the 55 kb plasmid, and derivatives thereof are preferred Lac$^+$ genetic elements for transforming a food-grade bacterium for the ability to ferment lactose.

Plasmids pTSL, pTSLP, and the 55 kb plasmid exhibit a lactose fermentation phenotype, and plasmids pTSLP and the 55 kb plasmid further exhibit an extracellular proteinase phenotype. The ability of these plasmids to confer lactose fermenting ability on a bacterial host depends on the expression of lactococcal lactose genes for the PTS enzymes EIII$^{lac}$, EII$^{lac}$, and phospho-β-galactosidase. Maintenance of these plasmids as extrachromosomal elements may involve expression of lactococcal genes needed for plasmid replication and/or copy control.

Food-grade bacteria containing pTSL, pTSLP, or the 55 kb plasmid or their derivatives are completely resistant to streptococcal and lactococcal phage and also have the ability to ferment milk. As a result of these properties, such food-grade bacteria containing these genetic elements are extremely useful in the production of cheese and other cultured dairy products. These bacteria are capable of more efficient fermentation since they are not sensitive to streptococcal and lactococcal phages that are present or are likely to be introduced into fermentation factories. These bacteria are useful in making starter cultures for the production of cheese and cultured dairy products. The preparation and use of starter cultures is well known in the art. Starter cultures can be formulated using food grade bacteria containing a Lac$^+$ genetic element instead of the lactococci or streptococci presently used. If it preferable in making a starter culture with food grade bacteria containing a Lac$^+$ genetic element according to the present invention to select the food grade bacteria to match the temperature preference of the bacteria being replaced. For example, if mesophilic lactococci are to be replaced with phage-resistant Lac$^+$ bacteria according to the present invention, the phage-resistant bacteria should also be mesophilic, such as *P. inopinatus, P. dextranicus*, or Leuconostoc spp. Similarly, if the bacteria being replaced are thermophilic, then the replacement phage-resistant bacteria should also be thermophilic, such as *P. acidilactici* and *P. pentosaceus*.

Derivatives of pTSL, pTSLP, and the 55 kb plasmid can be prepared by using techniques well known in the art. Thus, insertions and/or deletions to these plasmids can be made using standard techniques, such as are described in J. Sambrook et al., *Molecular Cloning: A Laboratory Manual* (2d ed., 1989); T. Maniatis et al., *Molecular Cloning: A Laboratory Manual* (1982); and F. Ausubel et al., *Current Protocols in Molecular Biology* (1987). Similarly, the plasmid-borne genetic determinants from these plasmids for lactose fermentation can be inserted into any other plasmid using conventional techniques, such as those described in Sambrook, supra, Maniatis, supra, and Ausubel, supra. A genetic determinant can first be isolated from pTSL, for example, and then inserted into another plasmid. The second plasmid can be further manipulated as needed. A pTSL genetic determinant for lactose fermentation can be isolated as follows. Restriction fragments of pTSL are isolated and then inserted into an appropriate plasmid for eventual propagation in a Lac⁻ strain. The recombinant plasmid is then inserted into the Lac⁻ bacterial strain, such as plasmid-cured, Lac⁻ *L. lactis* LM0230, and the transformed bacteria are analyzed for ability to grow with lactose as the sole carbon source. Colonies that grow on lactose contain the genetic determinants for lactose fermentation. The restriction fragment with this determinant can be further manipulated by conventional techniques.

In the following examples, stock cultures of bacteria were stored frozen at −70° C. in a medium containing 9% (v/v) milk and 11% (v/v) glycerol. Working cultures were kept at 4° C. in broth and maintained by biweekly transfer. Pediococci, lactobacilli, and Leuconostoc spp. were propagated in MRS (Difco Laboratories, Detriot, Mich.). Lactococci and streptococci were propagated in M17 broth, B. E Terzaghi & W. E. Sandine, *Improved Medium for Lactic Streptococci and Their Bacteriophages*, 50 Appl. Microbiol. 807–13 (1975), containing 0.5% (w/v) glucose or lactose as the sole carbohydrate source. Mesophilic species, such as *Pediococcus inopinatus*, *Lactococcus lactis*, Leuconostoc spp., and *Lactobacillus casei*, were propagated at 30° C., while "thermophilic" lactic acid bacteria, such as *P. acidilactici*, *Streptococcus thermophilus*, and *Lactobacillus helveticus* were incubated at 37° C.

Transformation of bacteria with plasmid DNA was performed by electroporation with a Bio-Rad "GENE PULSER" (Richmond, Calif.) or Prototype Design Services Model ZA1000 electroporation unit (Madison, Wis.).

EXAMPLE 1

A 35 kb derivative of the 55 kb lac plasmid of *Lactococcus lactis* C2 (National Collection of Food Bacteria; Berkshire, UK; strain NCFB 2031) was developed by transduction as described in L. L. McKay et al., *Transduction of Lactose Metabolism in Streptococcus lactis C2*, 115 J. Bacteriol. 810–15 (1973), hereby incorporated by reference. Prophage were induced from *L. lactis* C2 with ultraviolet radiation, as described by C. Park & L. L. McKay, *Induction of Prophage in Lactic Streptococci Isolated from Commercial Dairy Starter Cultures*, 38 J. Milk Food Technol. 594–97 (1975), hereby incorporated by reference, and transduction of naturally occurring C2 lac plasmid deletion derivatives to the plasmid-cured, Lac⁻ strain, *L. lactis* LM0230, was performed by the method of McKay, supra. Lac⁺ LM0230 transductants were identified on bromcresol purple (BCP)-lactose indicator plates, L. L. McKay et al., *Loss of Lactose Metabolism in Lactic Streptococci*, 23 Appl. Microbiol. 1090–96 (1972). The presence of the 35 kb lactose plasmid was established by electrophoresis in 0.6% agarose gels at 3 V/cm for 3 hours, e.g. Maniatis, supra.

EXAMPLE 2

The 35 kb lactose plasmid of Example 1 was isolated from a Lac⁺ transductant by the method of D. G. Anderson a L. L. McKay, *Simple and Rapid Method for Isolating Large Plasmid DNA from Lactic Streptococci*, 46 Appl. Environ. Microbiol. 549–552 (1983), hereby incorporated by reference. Plasmid DNA intended for electro-transformation was further purified by cesium chloride density gradient centrifugation, e.g., Maniatis, supra.

EXAMPLE 3

Pediococcus acidilacticiATCC 12697 cells were grown overnight in 10 ml of MRS broth (Difco Laboratories, Detroit, Mich.) containing 0.5M sorbitol. This overnight culture was used to inoculate 500 ml of MRS broth containing 0.5M sorbitol, 3% glycine, and 40 mM D-/L-threonine. The culture was then incubated 2–4 hours at 37° C. to an O.D.$_{600}$ of 0.4–0.5. The bacterial cells were then collected by centrifugation at 5000 rpm for 10 minutes. The cell pellet was resuspended in 25 ml of cold 0.5M sorbitol, 10% glycerol. The cells were then washed twice in the same medium by centrifuging the cells and resuspending the pellet, as described above. The final cell pellet was then resuspended in 1 mM K$_2$HPO$_4$, 1 mM MgCl$_2$, 0.5M sorbitol, 10% glycerol. An aliquot of 4 µl of the 35 kb lactose plasmid DNA (250 µg/ml), prepared as in Example 2, was mixed with 80 µl of cells and transferred to a 0.1 cm electroporation cuvette. The cells were then electroporated at 1.8 kV, 200 ohms, and 25 µF. Two ml of recovery medium, MRS containing 0.5M sorbitol, 20 mM MgCl$_2$, and 2 mM CaCl$_2$, was then added to the electroporated cells, and the mixture was incubated in an ice bath for 5 minutes and then incubated at 37° C. for 2 hours. The cells were then plated on BCP-lactose indicator agar containing 0.5M sorbitol. Plates were incubated for 48–72 hours and then examined for transformants.

The presence of plasmid DNA in these transformants was confirmed by preparing bacterial lysates and analysing the lysates by agarose gel electrophoresis, Maniatis, supra.

Lactose-positive transformants were then propagated in MRS containing 0.5% lactose as the sole carbon source.

EXAMPLE 4

*Pediococcus pentosaceus* ATCC 25744 and ATCC 25745 cells were transformed with 35 kb lactose plasmid DNA, prepared according to Example 2, by the procedure of Example 3. The results were substantially identical to those of Example 3.

EXAMPLE 5

*P. inopinatus* LMG 11409 and LMG 11410 are transformed with 35 kb lactose plasmid, prepared according to Example 2, by the procedure of Example 3.

EXAMPLE 6

*P. dextrinicus* (ATCC 33087) are transformed with 35 kb lactose plasmid, prepared according to Example 2, by the procedure of Example 3.

EXAMPLE 7

*Pediococcus acidilactici* ATCC 12697 was transformed with a Lac⁺ plasmid, pPN-1, according to the procedure of Example 3. Such transformant is designated herein as *P. acidilactici* (pPN-1). *P. acidilactici* ATCC 12697, *P. acidi-*

Figure 2:
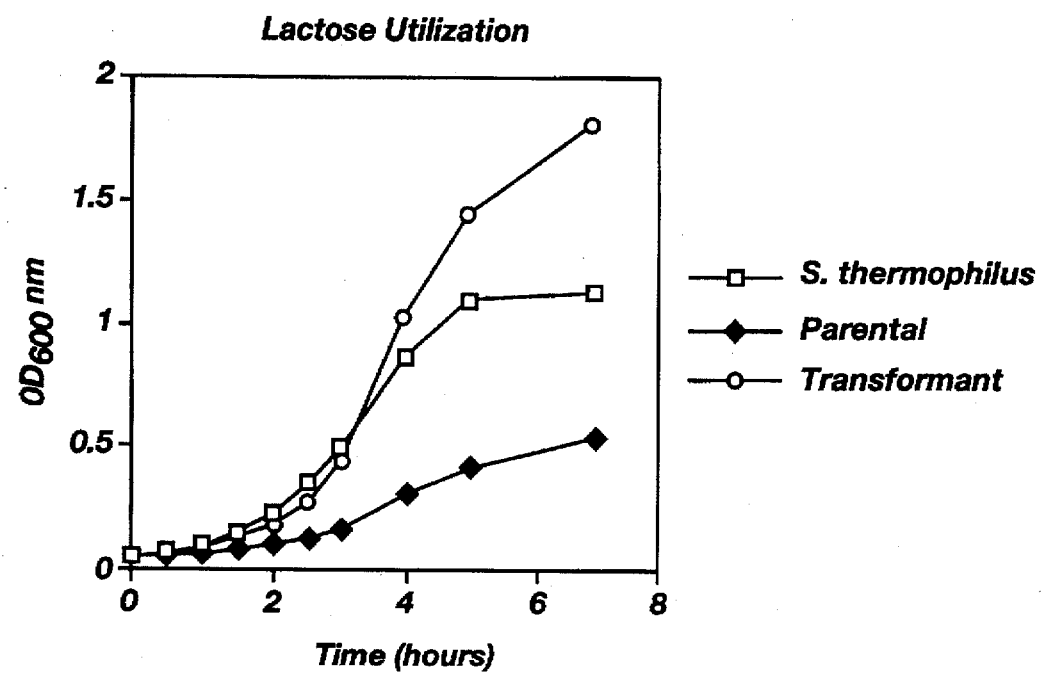
FIG. 2 shows utilization of lactose, as measured by optical density at 600 nm, as a function of time of growth: ◇—untransformed *P. acidilactici*; ○—Lac$^+$ transformant *P. acidilactici* (pPN-1); □—Lac$^+$ *S. thermophilus* control.
Figure 3:
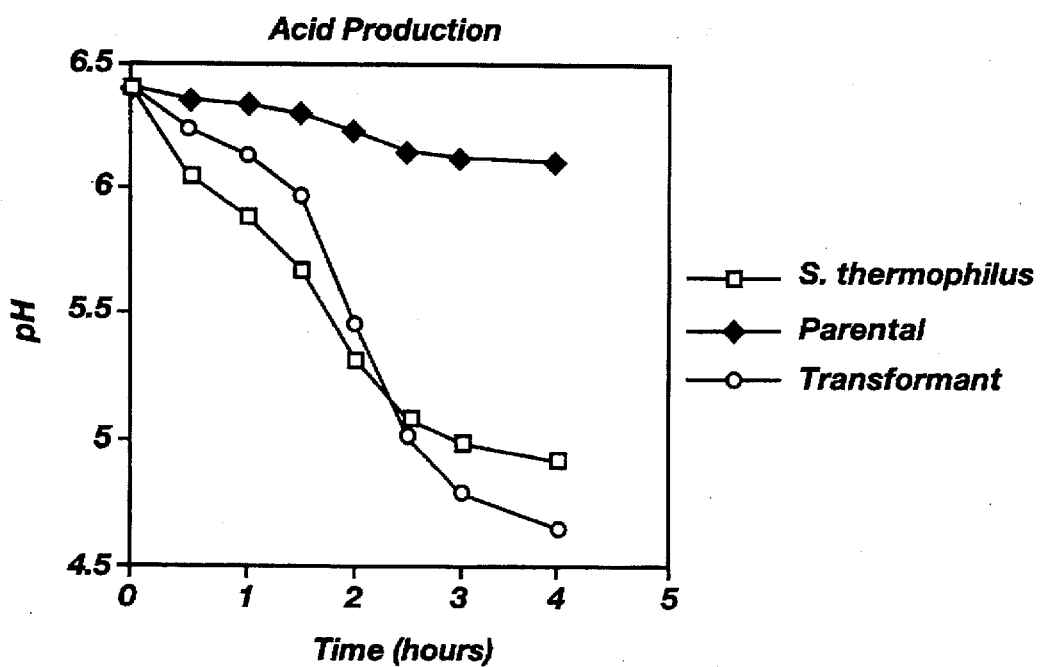
FIG. 3 shows the pH as a function of time for the cultures of FIG. 2.

*lactici* (pPN-1), and *Streptococcus thermophilus* TA061 were grown separately in modified MRS broth containing lactose in place of glucose. FIG. 2 shows utilization of lactose, as measured by optical density at 600 nm, as a function of time of growth. The untransformed parent *P. acidilactici* grew slowly, whereas the Lac$^+$ transformant *P. acidilactici* (pPN-1) grew much more rapidly on lactose, even outperforming the control *S. thermophilus*. FIG. 3 shows the pH change of the same cultures as a function of time. The untransformed parent *P. acidilactici* reduced the pH of the medium very little, whereas the Lac$^+$ transformant *P. acidilactici* (pPN-1) and the control *S. thermophilus* were about equal in acid production after 2 hours, but *P. acidilactici* (pPN-1) outperformed *S. thermophilus* by 3 hours and thereafter. This shows that a Lac$^-$ food grade bacterium can be transformed with a plasmid containing the genes of the lactococcus PTS system to result in Lac$^+$ bacteria that efficiently grow and produce acid by fermentation of lactose.

EXAMPLE 8

*P. acidilactici* strains ATCC 12697 and ATCC 23745 were transformed with a Lac$^+$ plasmid according to the procedure of Example 3. The resulting transformants were designated as strains 12697.1 and 23745.1. These transformed strains were sent to an independent testing laboratory where they were tested alongside tester bacterial strains for susceptibility to phage in whey samples routinely received from commercial plants during a one month period.

The test involves making serial dilutions of whey samples submitted for testing. Bacteriophage testing tubes are prepared by adding BCP, milk, and bacterial inoculum to a test tube. The diluted whey samples are then added to the bacteriophage testing tubes and mixed. The mixtures are then incubated at 30°–32° C. for 6 hours. A control tube that lacks whey and blank tubes that lack bacteria are also prepared. After incubation, the assay is interpreted by comparing the color of the tubes containing whey dilutions with the color of the control tube. A culture uninhibited by phage produces sufficient lactic acid to turn the color of the BCP from blue to yellow during the test period. Phage infection inhibits lactic acid production, which is indicated by a blue (full inhibition) to blue-green (partial inhibition) color in the test tube. The color also roughly indicates the phage concentration present in a whey sample.

The final report of the testing laboratory stated: "No bacteriophage were detected in one month of testing these two strains (12697.1 and 23745.1) against all whey samples received for the DSS meso and thermo cultures. This amounted to approximately 1670 BCP phage tests." This evidence shows that food grade bacteria transformed with a genetic element containing lactococcal PTS genes according to the instant invention are resistant to bacteriophage encountered in commercial dairy fermentations.

EXAMPLE 9

A starter culture, comprising a food grade bacterium transformed with a genetic element containing lactococcal PTS genes, for direct vat inoculation of milk is prepared as follows. An aqueous medium (450 gallons) containing 6% by weight of non-fat dry milk solids, 1% by weight of glucose, and 1% yeast extract is charged into a 500 gallon dairy processor. The medium is pasteurized at 90° C. for 60 minutes under constant agitation at 24 rpm, after which the medium is cooled to 26°–30° C. The medium is then inoculated with 2% by volume of an active subculture of genetically engineered, Lac$^+$ *Pediococcus dextrinicus* prepared according to Example 6.

The inoculated medium is then incubated for 10–12 hours at 26°–30° C. with constant agitation at 24 rpm and automatic pH control at pH 5.8 to 6.2. Concentrated ammonium hydroxide is used for pH neutralization. After 10–12 hours of incubation, the pH is adjusted to 6.4–6.8 with simultaneous cooling to 12°–16° C. and addition of 2% by weight of sodium hexametaphosphate. Agitation is increased to 48 rpm to effect dissolution of the sodium hexametaphosphate. After 30–60 minutes of mixing, the cooled culture medium is centrifuged on an automatic desludging CIP separator. The culture is fed at 600 gallons per hour to the separator. The automatic desludging is adjusted to give a 5% by volume yield of concentrate based upon the total feed volume.

EXAMPLE 10

Mozzarella cheese is made with a food grade bacterium transformed with a genetic element containing lactococcal PTS genes by a process involving the following steps:

(a) pasteurizing cow's milk having a fat content in the range of about 1.5 to 3.5% by weight;

(b) fermenting the milk with *Pediococcus acidilactici* transformed with pTSL to obtain a cheese milk;

(c) coagulating the cheese milk to obtain a coagulum comprised of curd and whey;

(d) cutting the coagulum and draining the whey therefrom, thereby leaving a cheese curd;

(e) heating, kneading, and stretching the cheese curd until it is a homogeneous, fibrous mass having a moisture content in the range of about 45 to 60% by weight and a milkfat content of at least about 30% by weight on a dried solids basis;

(f) placing the mass in a bath of cold brine and leaving it there long enough to achieve cooling and salt penetration; and (g) removing the cooled cheese from the brine. After the brining step, the resultant unripened mozzarella cheese is aged at about 35° F. to 45° F. for about 7 to 21 days to develop characteristic taste, texture, and acceptable baking properties. After aging, the mozzarella cheese is comminuted and frozen, thereby halting the ripening processes, and then stored in refrigerated containers.

We claim:

1. A method of making a phage resistant starter culture for fermenting milk comprising transforming a food-grade bacterium that lacks a lactose-fermenting phenotype and is resistant to lactococcal and streptococcal phages with a genetic element bearing a genetic locus for lactose fermentation to result in a transformed food-grade bacterium that is operable for replicating said genetic element, expresses a lactose fermentation phenotype, and bears no antibiotic resistance marker.

2. The method of claim 1 wherein said food-grade bacterium is a member selected from the group consisting of *Pediococcus acidilactici, Pediococcus dextrinicus, Pediococcus inopinatus, Pediococcus halophilus, Pediococcus damnosus, Pediococcus pentosaceus, Leuconostoc cremoris, Leuconostoc citrovorum, Leuconostoc dextranicum,* and *Leuconostoc mesenteroides*.

3. The method of claim 2 wherein said genetic element encodes lactose-specific components of a lactococcal phosphotransferase system.

4. The method of claim 3 wherein said lactococcal phosphotransferase system is derived from *Lactococcus lactis*.

5. The method of claim 4 wherein said genetic element contains no antibiotic resistance marker and is a member selected from the group consisting of a plasmid, cosmid, phagemid, lysogenic virus, non-lytic virus, transposable element, and mixtures thereof.

6. The method of claim 5 wherein said genetic element is a plasmid.

7. The method of claim 6 wherein said plasmid is a member selected from the group consisting of the *Lactococcus lactis* C2 55 kb plasmid and lac$^+$ derivatives thereof.

8. The method of claim 7 wherein said plasmid is pTSL.

9. The method of claim 7 wherein said plasmid is pTSLP.

10. The method of claim 7 wherein said plasmid is the *Lactococcus lactis* C2 55 kb plasmid.

11. A method of making a phage-resistant starter culture for fermenting milk comprising mixing a culture of food-grade bacteria that lack a lactose-fermenting phenotype and are resistant to lactococcal and streptococcal phages with an effective amount of a genetic element bearing a genetic locus for lactose fermentation to form a mixture, wherein neither the food-grade bacteria nor the genetic element bear an antibiotic resistance marker; treating the mixture such that a portion of the food-grade bacteria is transformed with the genetic element to result in a mixture of transformed and untransformed bacteria; and selecting bacteria transformed with the genetic element from the mixture of transformed and untransformed bacteria by ability to grow on lactose as a sole carbon source.

* * * * *